United States Patent
Nishida et al.

(10) Patent No.: US 9,030,654 B2
(45) Date of Patent: May 12, 2015

(54) CONCENTRATION DETERMINATION APPARATUS AND CONCENTRATION DETERMINATION METHOD FOR MEASURING A CONCENTRATION OF A MEASURED COMPONENT CONTAINED IN A LIVING BODY TISSUE

(75) Inventors: Kazuhiro Nishida, Matsumoto (JP); Kazuhiko Amano, Tokyo (JP); Koichi Shimizu, Sapporo (JP)

(73) Assignees: Seiko Epson Corporation, Tokyo (JP); National University Corporation Hokkaido University, Hokkaido (JP)

( * ) Notice: Subject to any disclaimer, the term of this patent is extended or adjusted under 35 U.S.C. 154(b) by 336 days.

(21) Appl. No.: 13/493,384

(22) Filed: Jun. 11, 2012

(65) Prior Publication Data

US 2012/0330110 A1 Dec. 27, 2012

(30) Foreign Application Priority Data

Jun. 21, 2011 (JP) ................. P2011-137316

(51) Int. Cl.
*A61B 5/01* (2006.01)
*A61B 5/145* (2006.01)
*A61B 5/1455* (2006.01)

(52) U.S. Cl.
CPC .............. *A61B 5/01* (2013.01); *A61B 5/1455* (2013.01); *A61B 5/14532* (2013.01)

(58) Field of Classification Search
CPC .............. A61B 5/01; A61B 5/14532; G01N 2021/174; G01N 2021/1742; G01N 2021/0744; G01N 2021/3125; G01N 2001/2826

USPC .......... 600/301, 309, 310, 316; 356/432, 433, 356/434, 435–444, 72
See application file for complete search history.

(56) References Cited

U.S. PATENT DOCUMENTS

| | | | |
|---|---|---|---|
| 5,750,994 A | 5/1998 | Schlager | |
| 7,079,252 B1 | 7/2006 | Debreczeny et al. | |
| 2004/0142402 A1* | 7/2004 | Maruo et al. | 435/14 |
| 2007/0027373 A1* | 2/2007 | Xie | 600/316 |
| 2008/0186483 A1* | 8/2008 | Kiesel et al. | 356/246 |
| 2010/0016689 A1* | 1/2010 | Kanayama et al. | 600/316 |
| 2010/0256920 A1 | 10/2010 | Amano et al. | |

(Continued)

FOREIGN PATENT DOCUMENTS

| | | |
|---|---|---|
| JP | H09-159606 A | 6/1997 |
| JP | 2000-258344 A | 9/2000 |

(Continued)

*Primary Examiner* — Michael Stafira
*Assistant Examiner* — Michael P Lapage
(74) *Attorney, Agent, or Firm* — Oliff PLC

(57) ABSTRACT

A first temperature sensor is formed in a first measurement area. A first input part is formed in the first measurement area so that an output surface thereof is exposed to the inner surface of the liquid tank. A first light receiving part receives a reference light through the liquid from the first input part. A second input part causes a second incident light to be incident on a living body. A second light receiving part receives a measurement light from the second input part. Based on the light intensity of the reference light and the measurement light, an absorbance calculation device can detect the absorbance of the liquid and living body tissue. A concentration calculation device compares the absorbance of the liquid with the absorbance of the living body tissue and calculates a concentration of a measured component contained in the living body tissue.

13 Claims, 11 Drawing Sheets

(56) References Cited

U.S. PATENT DOCUMENTS

| 2010/0280348 | A1* | 11/2010 | Wenzel et al. | 600/365 |
| 2012/0010477 | A1 | 1/2012 | Amano et al. | |
| 2012/0242979 | A1 | 9/2012 | Nishida et al. | |
| 2014/0058226 | A1* | 2/2014 | Chernobrod et al. | 600/316 |

FOREIGN PATENT DOCUMENTS

| JP | A-2001-299727 | 10/2001 |
| JP | A-2003-535329 | 11/2003 |
| JP | A-2010-237139 | 10/2010 |
| JP | A-2011-153921 | 8/2011 |
| JP | A-2011-167257 | 9/2011 |
| JP | A-2012-019833 | 2/2012 |
| JP | A-2012-019834 | 2/2012 |
| JP | A-2012-021811 | 2/2012 |
| JP | A-2012-021812 | 2/2012 |
| JP | A-2012-200277 | 10/2012 |
| JP | A-2013-53864 | 3/2013 |
| JP | A-2013-64631 | 4/2013 |

* cited by examiner

CONCENTRATION DETERMINATION APPARATUS AND CONCENTRATION DETERMINATION METHOD FOR MEASURING A CONCENTRATION OF A MEASURED COMPONENT CONTAINED IN A LIVING BODY TISSUE

BACKGROUND OF THE INVENTION

1. Technical Field

The present invention relates to a concentration determination apparatus and a concentration determination method that are suitable for a determination of a concentration of a measured component contained in a living body tissue, particularly, a concentration of glucose contained in skin.

This application claims priority to and the benefits of Japanese Patent Application No. 2011-137316 filed on Jun. 21, 2011, the disclosure of which being incorporated herein by reference.

2. Related Art

Traditionally, measurement of a blood sugar level has been performed by taking a blood sample from, for example, a fingertip and measuring enzyme activity for glucose in the blood. However, in such a method of measuring a blood sugar level, blood must be collected from, for example, the fingertip to perform the measurement and taking the blood sample requires effort and is painful. Also, a measurement tip for adhering blood is necessary. Accordingly, there is a need for a non-invasive blood sugar level measurement method that does not require that a blood sample be taken.

For example, an apparatus for measuring a glucose concentration in a living body disclosed in Japanese Patent Application, First Publication No. 2001-29972 has been known as an example of realizing the non-invasive blood sugar level measurement as described above. In general, an apparatus in which, when near-infrared spectroscopic analysis of a solution or a sample having high moisture content is performed, for example, a shift of a spectrum of the sample due to temperature change is greatly changed, similar to a spectrum of water, and an influence of temperature is not negligible in quantitative analysis has been known. In the measurement apparatus disclosed in Japanese Patent Application, First Publication No. 2001-299727, when a glucose concentration is measured, a temperature of a target tissue is controlled to have a constant value by a temperature control means, thereby quantifying the target component with higher measurement accuracy.

Further, for example, a double-beam Fourier transform infrared spectroscopic method for detecting a specific component in a sample having low transmittance disclosed in Published Japanese Translation of a PCT application No. 2003-535329 has been known. In the above-described infrared spectroscopic analysis, arranging a material containing water as a reference material for a measuring object is shown. Accordingly, the target component may be quantified with higher measurement accuracy.

SUMMARY OF THE INVENTION

However, in the measurement apparatus disclosed in Japanese Patent Application, First Publication No. 2001-299727, there is no reference material for a measuring object when measurement is performed. Accordingly, a deviation (error) is easily generated in a measurement value measured by the above measurement apparatus. Further, when a concentration of a very small amount of component is detected, it is necessary to detect a small absorbance from a great absorbance measurement value. Accordingly, it is difficult to increase the measurement accuracy, and a large dynamic range is necessary for measurement with high accuracy. Further, the measurement apparatus includes a temperature control means formed on a measurement surface. However, for example, when a glucose concentration is measured in a living body tissue, it is difficult to secure temperature control accuracy in the order of 0.001° C. necessary for the measurement.

Further, in the infrared spectroscopic analysis method disclosed in Published Japanese Translation of a PCT application No. 2003-535329, a reference material for a measuring object is arranged. However, when there is a difference in temperature between the reference material and a sample of the measuring object, a spectrum is shifted due to a temperature change, which causes an error in the measurement value. As a result, in the infrared spectroscopic analysis method disclosed in Published Japanese Translation of a PCT application No. 2003-535329, it is also difficult to perform quantification with high accuracy.

The present invention has been made in view of the above-described problem, and one aspect of the present invention relates to a concentration determination apparatus capable of performing highly accurate measurement and rapid measurement of a concentration of a measured component contained in a living body tissue without being affected by a temperature change in a measurement environment.

Further, one aspect of the present invention relates to a concentration determination method by which highly accurate measurement and rapid measurement of a concentration of a measured component contained in a living body tissue can be performed without being affected by a temperature change in a measurement environment.

In order to resolve the above-described problem, some aspects of the present invention provide the following concentration determination apparatus and method.

The concentration determination apparatus of the present invention includes a storage body for holding liquid, a temperature control plate constituting the storage body and having one surface forming a closely contacted surface which is closely contacted to a living body tissue and another surface forming a liquid contact surface brought into contact with the liquid, a first input part for causing a first incident light to be incident on the storage body, a first light receiving part for receiving a reference light transmitted through the liquid from the first input part, a second input part for causing a second incident light to be incident on the living body tissue, a second light receiving part for receiving a measurement light from the second input part via the living body tissue, a temperature detection device for detecting a temperature of the liquid and a temperature of the living body tissue, an absorbance calculation device for detecting an absorbance of the liquid and an absorbance of the living body tissue based on a light intensity of the reference light and a light intensity of the measurement light, and a concentration calculation device for comparing the absorbance of the liquid with the absorbance of the living body tissue and calculating a concentration of a measured component contained in the living body tissue.

According to the above-described concentration determination apparatus, the liquid that is the reference material is stored in the storage body, which stores the liquid, and the absorbance of the reference light transmitted through the liquid is referenced with respect to the absorbance of the measurement light back-scattered from the living body tissue that is the measuring object, thereby obtaining an accurate absorbance without being affected by the liquid (e.g., water) contained in the measuring object.

Further, the temperature control plate having excellent thermal conductivity is formed in at least part of the storage body that contacts with the measuring object, and the temperature of the liquid in the storage body rises due to heat of the living body tissue that is the measuring object through the temperature control plate, such that the temperature of the liquid can be rapidly the same as the temperature of the living body tissue. Accordingly, even when the liquid is liquid whose absorption is sensitive to a temperature, the temperature of the liquid that is the reference material is the same as the temperature of the living body tissue that is the measuring object (i.e., a thermal equilibrium state) and then the absorbance is measured. Thus, it is possible to eliminate a measurement error caused by an influence of the liquid in the living body tissue due to a temperature change and perform an accurate concentration determination for the measured material.

The liquid is water or liquid corresponding to body fluid whose component configuration is obvious. Also, the liquid may be a liquid having a scattering characteristic.

The temperature control plate may include a thermal conductor for causing the body temperature of the living body tissue and the liquid temperature of the liquid to be heat-exchanged with each other.

The storage body may further include a reflector for reflecting the first incident light incident from the first input part to the first light receiving part. Also, the concentration determination apparatus may include a light source unit including a plurality of light sources.

The storage body may further include a temperature control device for heating or cooling the liquid.

The concentration determination apparatus further includes a light source unit including a light source, and a spectroscopic device for dividing light irradiated from the light source toward the first input part and the second input part.

The concentration determination apparatus further includes one light receiving element for measuring both the light intensity of the reference light incident on the first light receiving part and the light intensity of the measurement light incident on the second light receiving part.

An optical path length for the reference light from the first input part to the first light receiving part may be the same as an optical path length for the measurement light from the second input part to the second light receiving part.

A concentration determination method of the present invention is a concentration determination method using a concentration determination apparatus comprising a storage body for holding liquid, a temperature control plate constituting the storage body and having one surface forming a closely contacted surface which is closely contacted to a living body tissue and the other surface forming a liquid contact surface brought into contact with the liquid, a first input part for causing a first incident light to be incident on the storage body, a first light receiving part for receiving a reference light transmitted through the liquid from the first input part, a second input part for causing a second incident light to be incident on the living body tissue, a second light receiving part for receiving a measurement light from the second input part via the living body tissue, a temperature detection device for detecting a temperature of the liquid and a temperature of the living body tissue, an absorbance calculation device for detecting an absorbance of the liquid and an absorbance of the living body tissue based on a light intensity of the reference light and a light intensity of the measurement light, and a concentration calculation device for comparing the absorbance of the liquid with the absorbance of the living body tissue and calculating a concentration of a measured component contained in the living body tissue, wherein: the measurement light is light from the second incident light back-scattered in the living body tissue, and the method comprises processes of:

equilibrating the temperatures so that a difference between the body temperature of the living body tissue and the liquid temperature of the liquid is within 0.1° C.; measuring the absorbance of the liquid based on the light intensity of the reference light; measuring the absorbance of the living body tissue based on the light intensity of the measurement light; and using the absorbance of the liquid as a reference and calculating the concentration of the measured component contained in the living body tissue from the absorbance of the living body tissue.

The first incident light and the second incident light may be short pulsed lights.

EMBODIMENTS OF THE INVENTION

Figure 1:
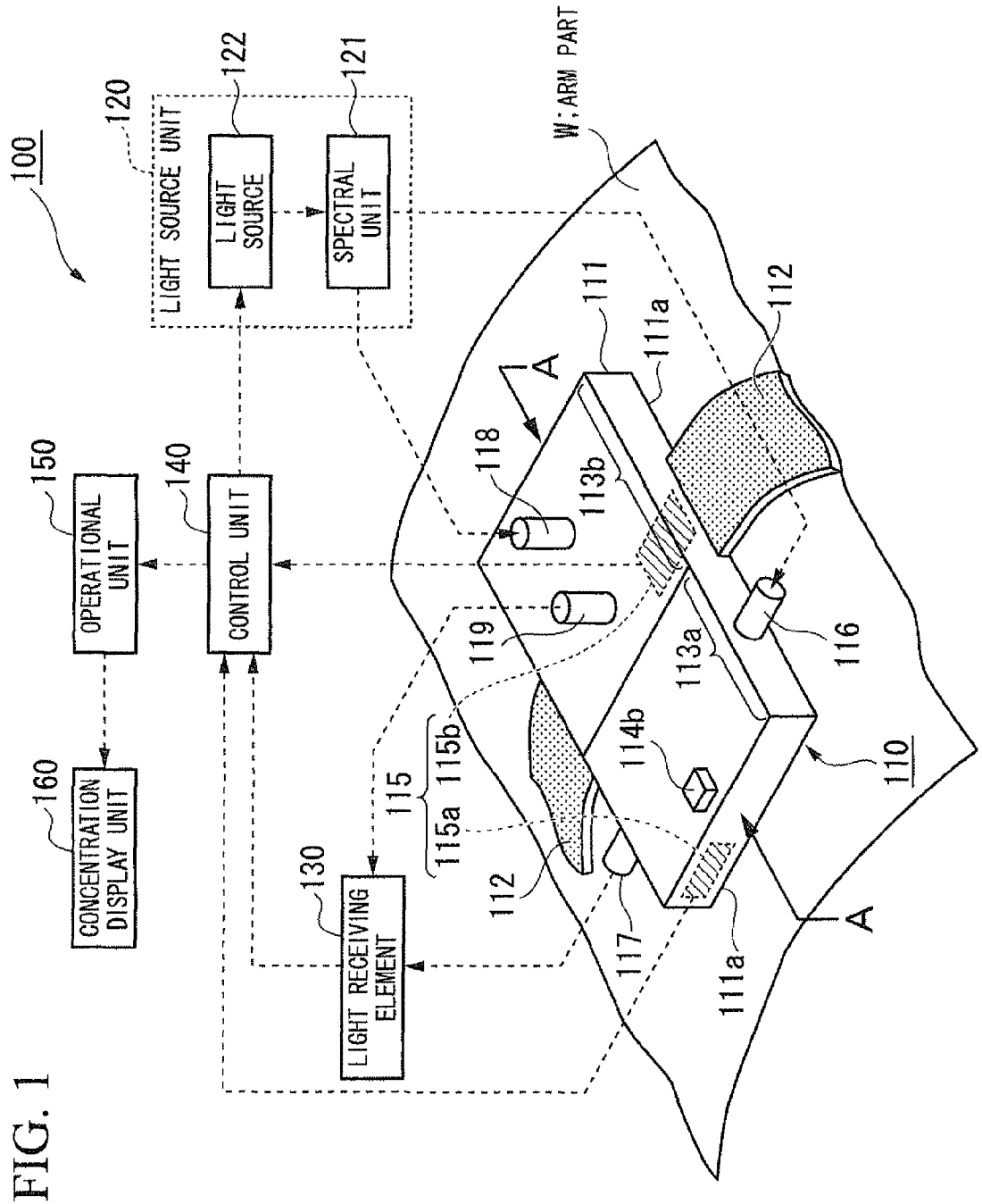
FIG. 1 is a schematic block diagram showing a configuration of a concentration determination apparatus.

Hereinafter, embodiments of a concentration determination apparatus and a concentration determination method according to the present invention will be described with reference to the accompanying drawings. Further, the following embodiments will be described in detail for better understanding of the present invention and do not limit the present invention unless mentioned otherwise. In the drawings used in the following description, for convenience, primary parts may be enlarged for easy understanding of characteristics of the present invention, and the dimensions of components may not be the same as actual ones.

(First Embodiment)

FIG. 1 is a schematic block diagram showing a configuration of a blood sugar level measurement apparatus, which is an example of a concentration determination apparatus.

The blood sugar level measurement apparatus (a concentration determination apparatus) 100 includes a measurement device 110, a light source unit 120, a light receiving element 130, a control unit 140, an operational unit 150, and a concentration display unit 160.

The measurement device 110 is mounted on, for example, an arm part of a human body and then used. The measurement device 110 includes a body part 111, and a band (fixing member) 112 for closely contacting and fixing the body part 111 to the arm part when glucose, which is a measuring object material, is measured.

The body part 111 has, for example, an overall appearance as a thin cube. In the body part 111, a first measurement area 113a is formed at one side from near a center of the body part 111 and a second measurement area 113b is formed at the other side.

Figure 2A:
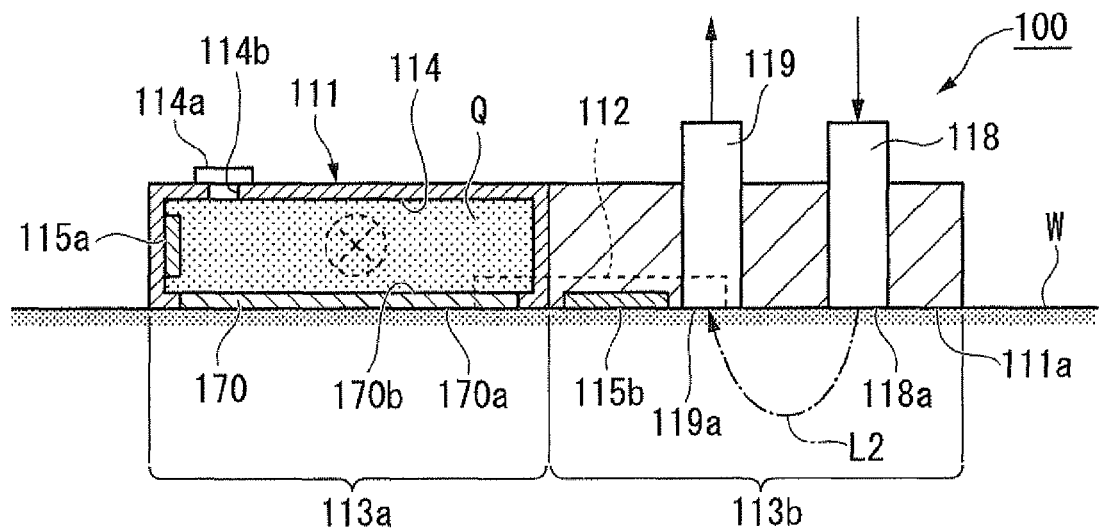
FIG. 2A is a cross-sectional view of a body part taken along line A-A in FIG
Figure 2B:
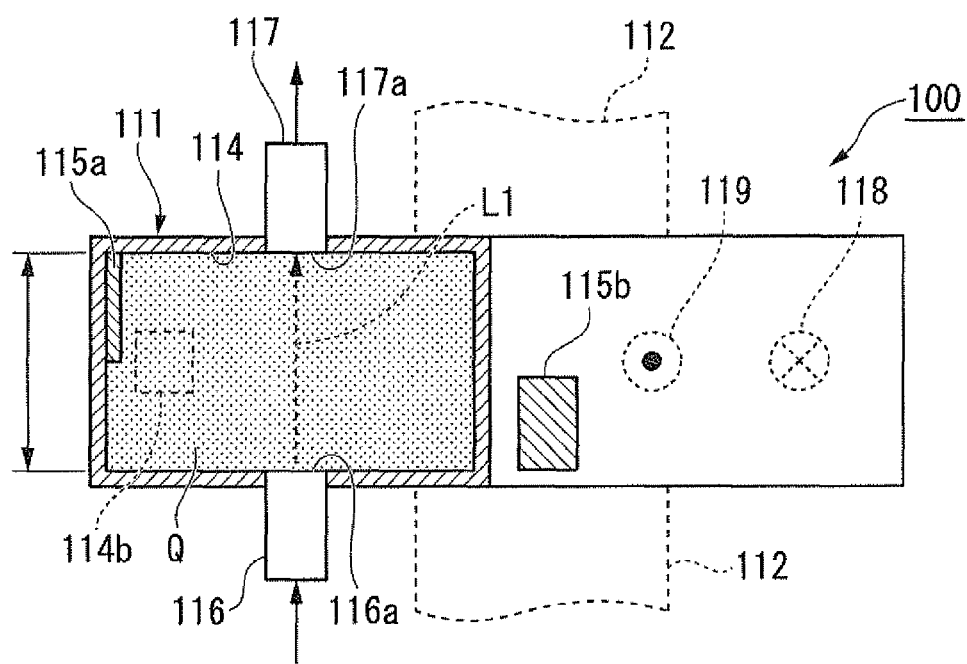
FIG. 2B is a plan view of the body part in FIG. 1 when viewed from above.

FIG. 2A is a cross-sectional view taken along line A-A of the body part 111 shown in FIG. 1. FIG. 2B is a plan view of the body part 111 shown in FIG. 1 when viewed from above.

For example, a hollow liquid tank (storage body) 114 that liquid (reference material) Q can be injected into and held in is formed in the first measurement area 113a. An opening 114a through which the liquid (reference material) Q is injected into or discharged from the liquid tank 114, and a stopper 114b for blocking the opening 114a are included in the first measurement area 113a.

A temperature control plate 170 is formed at a side of a bottom surface among wall surfaces partitioning the liquid tank (storage body) 114. In the temperature control plate 170, one surface thereof forms a closely contacted surface. 170a that is closely contacted to a surface of the living body tissue (e.g., the arm part W of the human body) that is the measuring object upon measurement, and the other surface thereof forms a liquid contact surface 170b that contacts the liquid (the reference material) Q. The temperature control plate 170 may be formed of a thermal conductor for efficiently heat-exchanging a body temperature of the living body tissue and a liquid temperature of the liquid Q with each other, such as a copper plate, an aluminum plate, or the like.

A first temperature sensor 115a is formed in the first measurement area 113a so that a measurement surface thereof is exposed to an inner surface of the liquid tank (storage body) 114. The first temperature sensor 115a detects a temperature T1 of the liquid Q injected into the liquid tank 114.

A first input part 116 is formed in the first measurement area 113a so that an output surface 116a of the first input part 116 is exposed to the inner surface of the liquid tank 114. The first input part 116 may be, for example, a light guiding member (a light guide) formed of transparent resin. The first input part 116 is optically connected to a light source 122 via a spectral unit (spectroscopic device) 121 of the light source unit 120. For example, the spectral unit 121 and the first input part 116 may be connected to each other by an optical fiber.

In the first measurement area 113a, a first light receiving part 117 is formed so that an input surface 117a thereof is exposed to the inner surface of the liquid tank 114. The first light receiving part 117 is formed in a position in which the input surface 117a faces the output surface 116a of the first input part 116. Accordingly, light output from the output surface 116a proceeds along one surface of the body part 111, for example, the liquid contact surface 170b, is transmitted through the liquid Q stored in the liquid tank 114, and is incident on the facing input surface 117a as a reference light L1.

The first light receiving part 117, for example, may be a light guiding member (light guide) formed of transparent resin. The first light receiving part 117 is optically connected to the light receiving element 130. The light receiving element 130 and the first light receiving part 117 are connected to each other, for example, by an optical fiber.

In the second measurement area 113b, a second temperature sensor 115b exposed to the bottom surface 111a of the body part 111 is formed to be brought into contact with the arm part W of the human body fixed to the band (fixing member) 112 upon measurement. The second temperature sensor 115b detects a surface temperature (a body temperature) T2 of the arm part W, which is the living body tissue of the measuring object. A temperature sensor 115 includes the second temperature sensor 115b and the first temperature sensor 115a.

A second input part 118 is formed in the second measurement area 113b so that an output surface 118a thereof is exposed to the bottom surface 111a of the body part 111. The second input part 118 may be, for example, a light guiding member (light guide) formed of transparent resin. The second input part 118 is optically connected to the light source 122 via the spectral unit 121 of the light source unit 120. The spectral unit 121 and the second input part 118 may be connected to each other, for example, by an optical fiber.

A second light receiving part 119 is formed in the second measurement area 113b so that an input surface 119a thereof is exposed to the bottom surface 111a of the body part 111. The input surface 119a of the second light receiving part 119 and the output surface 118a of the second input part 118 may be formed to extend on the same surface along the bottom surface 111a. Light output from the output surface 118a is incident on the arm part W, which is the living body tissue of the measuring object, output from the arm part W by backscattering, and incident on the input surface 119a parallel to the output surface 118a as a measurement light L2.

The second light receiving part 119 may be, for example, a light guiding member (light guide) formed of transparent resin. The second light receiving part 119 is optically connected to the light receiving element 130. The light receiving element 130 and the second light receiving part 117 may be connected to each other, for example, by an optical fiber.

The description will be further given with reference to FIG. 1. The light source unit 120 includes the light source 122 and the spectral unit (a spectroscopic device) 121. The light source 122 may be, for example, a laser light source that can irradiate a short pulsed light having a specific wavelength. Further, the short pulsed light refers to a pulsed light having a pulse width of about 100 psec or less. A pulsed light having a pulse width ranging from 0.1 psec to a few psec may be used as the short pulsed light.

The spectral unit (spectroscopic device) 121 includes, for example, an optical path switching device. The spectroscopic unit causes a light irradiated from the light source 122 to be selectively incident on the first input part 116 or the second input part 118. The spectral unit (spectroscopic device) 121 may include a prism, a half mirror, or the like, and may cause the light irradiated from the light source 122 to be divided and incident on the first input part 116 and the second input part 118.

The light receiving element 130 includes, for example, a photodiode. The light receiving element 130 transmits a light intensity signal according to a light intensity of the reference light L1 output from the first light receiving part 117 or the measurement light L2 output from the second light receiving part 119, to the control unit 140.

A mechanism for selectively receiving any one of the reference light L1 output from the first light receiving part 117 and the measurement light L2 output from the second light receiving part 119 under control of the control unit 140 may be further included.

The control unit 140 is connected to the light source unit 120, the temperature sensor 115, the light receiving element 130, and the operational unit 150. The control unit 140 includes an input/output circuit for transmitting and receiving signals, control information or the like to and from such units.

The operational unit 150 includes a CPU, a memory and the like, and may be, for example, a personal computer (PC). The operational unit 150 calculates a concentration of the measuring object, for example, based on light intensity information output from the control unit 140 or reference data stored in the memory in advance according to a predetermined procedure. Further, a detailed configuration of the operational unit 150 and the concentration calculation will be described later.

The concentration display unit 160 may be, for example, a display, a printer or the like. The concentration display unit 160 displays or prints the concentration of the measuring object calculated by the operational unit 150.

The spectral unit (spectroscopic device) 121 includes, for example, a diffraction grating. The spectroscopic unit may divide light irradiated from the light source 122 into wavelengths. A light having the wavelength selected by the spectral unit 121 is simultaneously incident on the first input part 116 and the second input part 118. When data acquisition for a plurality of wavelengths is necessary, lights having the divided different wavelengths may be sequentially incident on the first input part 116 and the second input part 118.

In another configuration example of the blood sugar level measurement apparatus (concentration determination apparatus) 100 shown in FIG. 1, the light source unit may include a plurality of light sources, for example, two light sources. A light emitted from one light source may be simultaneously incident on the first input part 116 and the second input part 118 and data acquisition may be performed. Then, a light emitted from the second light source may be simultaneously incident on the first input part 116 and the second input part 118 and data acquisition may be performed. Accordingly, even when the light source that emits a short pulsed light is a general light source for outputting a single wavelength light, it is possible to cause different wavelength lights to be incident on the first and second input parts with a simple configuration having no spectral unit (spectroscopic device) 121 by combining a plurality of light sources having different output wavelengths.

A concentration determination method using the blood sugar level measurement apparatus (the concentration determination apparatus) having the above configuration and an operation of the blood sugar level measurement apparatus will be described in detail.

First, prior to measurement of the blood sugar level, the user opens the stopper 114b of the liquid tank 114 formed in the body part 111 of the blood sugar level measurement apparatus 100 to cause the opening 114a to be exposed. Also, the user fills the liquid tank 114 with liquid as a reference material, specifically, water, from the opening 114a and then blocks the opening 114a with the stopper 114b. Further, this liquid may be body fluid collected in advance, liquid corresponding to body fluid whose components are obvious, a physiological salt solution, liquid having a scattering characteristic, or the like, as well as the water.

Next, the user closely contacts the bottom surface 111a of the body part 111 to a measurement place, for example, the arm part W, and fixes the body part 111 to the arm part using the band (fixing member) 112. Accordingly, the closely contacted surface 170a of the temperature control plate 170 is closely contacted to the surface of the arm part W. Also, the user waits a predetermined time, specifically, until a body temperature of the arm part W in contact with the closely contacted surface 170a of the temperature control plate 170 and a liquid temperature of the liquid Q in contact with the liquid contact surface 170b of the temperature control plate 170 are heat-exchanged through the temperature control plate 170 and then the liquid temperature of the liquid Q is heated or cooled to be the same as the body temperature, in a state in which the user causes the closely contacted surface 170a to be closely contacted to the arm part W.

The temperature of the liquid Q and the body temperature of the arm part are always measured by the temperature sensor 115 while the user is waiting. Specifically, temperature signals from the temperature sensor 115a for measuring the temperature of the liquid Q in the liquid tank 114 and the temperature sensor 115b closely contacted to the surface of the arm part W to measure the body temperature of the human body (the temperature of the skin surface that is the measurement place) are continuously input to the control unit 140. Also, if the temperature signal from the temperature sensor 115a and the temperature signal from the temperature sensor 115b become the same as each other in a predetermined range, it is determined that the temperature of the liquid Q in the liquid tank 114 rises due to the body temperature of the human body and the temperature of the liquid Q and the temperature of the skin surface have become the same as each other.

After the temperature of the liquid Q has become the same as that of the skin surface, the process proceeds to a measurement (determination) process for a blood sugar level. In the measurement (determination) process for a blood sugar level, a process of irradiating a short pulsed light to the skin, which is the measuring object, to measure an absorbance of the skin (a process of obtaining a measurement light), and a process of irradiating a short pulsed light to the liquid (water), which is a reference material, to measure an absorbance of the liquid (a process of obtaining a reference light) are performed with a predetermined time difference or simultaneously.

Figure 3:
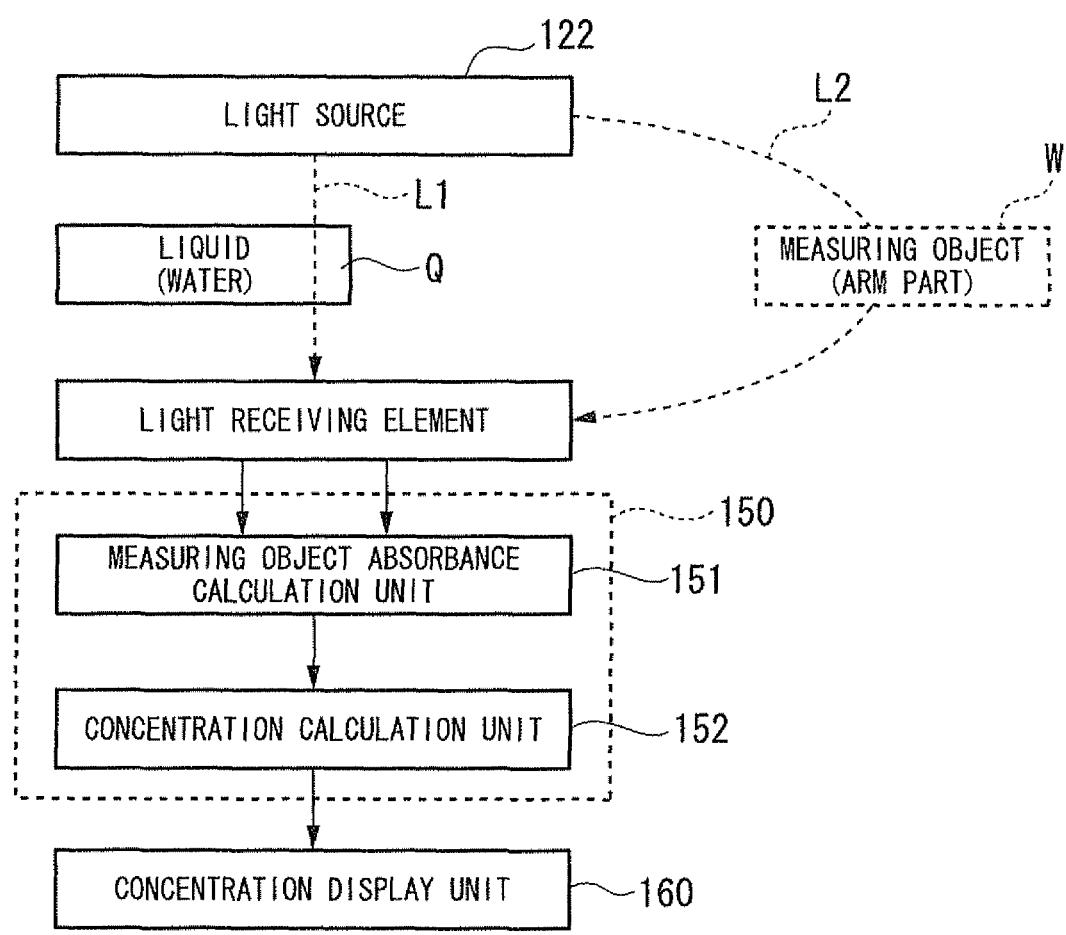
FIG. 3 is a configuration diagram showing a large flow of concentration determination.

FIG. 3 is a configuration diagram showing an example of the concentration determination, that is, a large flow of non-invasively measuring a glucose concentration in body fluid present in the skin of the arm part of the human body. The light output from the light source 122 is divided into two optical paths. In one optical path, the light is incident from the second input part 118 to the living body tissue that is the measuring object, that is, the arm part W of the human body to which the body part 111 has been fixed.

Figure 4:
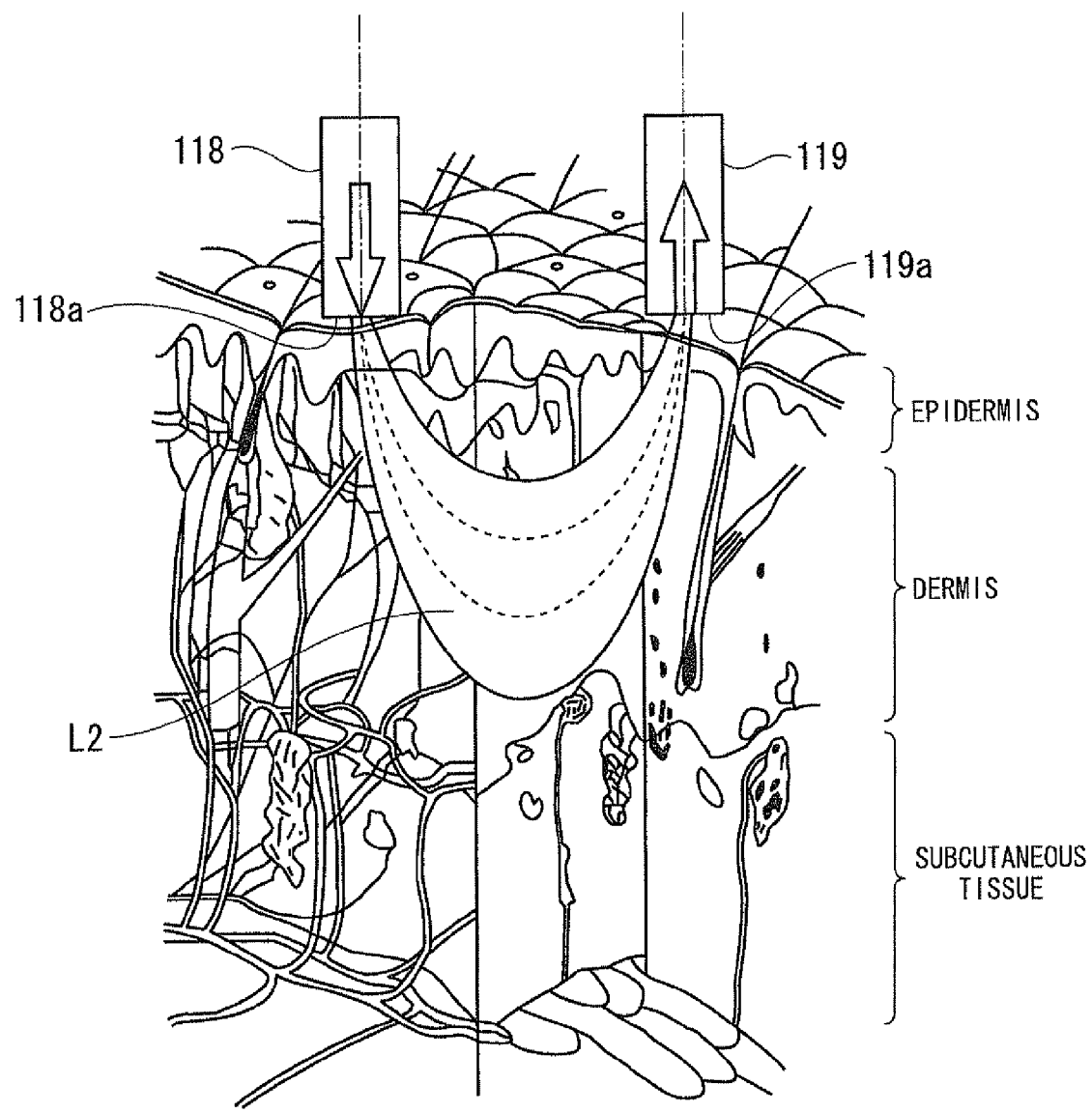
FIG. 4 is a schematic view of a skin tissue of a human and back-scattering of an incident light.

As shown in FIG. 4, skin tissue of a human is formed of three layers of an epidermis, a dermis, and subcutaneous tissue. The epidermis is an outermost thin layer having a thickness of 0.2 to 0.3 mm, and includes a corneous layer, a granular layer, a stratum spinosum, a bottom and the like. The dermis is a layer having a thickness of 0.5 to 2 mm, which is present between the epidermis and the subcutaneous tissue. In the dermis, there are nerves, hair roots, sebaceous glands or sweat glands, hair follicles, blood vessels, and lymph nodes. The subcutaneous tissue is a layer having a thickness of 1 to 3 mm, which is present beneath the dermis. Most of the subcutaneous tissue is formed of subcutaneous fat.

Capillaries and the like are developed in the dermis, rapid material movement according to blood glucose occurs, and a glucose concentration in the dermis is changed with blood glucose concentration (a blood sugar level). Therefore, the blood sugar level measurement apparatus 100 measures an absorbance after transmission through the measuring object by irradiating a light (a short pulsed light) from the second input part 118 to the surface of the skin tissue and detecting the measurement light L2 back-scattered from the light transmitted through the skin tissue and diffused, using the light receiving element 130 via the second light receiving part 119.

A light (short pulsed light) from the first input part 116 is incident on the liquid tank 114 filled with the liquid Q, which is the reference material, for example, water. The reference light L1 transmitted through the liquid Q is detected by the light receiving element 130 via the first light receiving part 117 to thereby measure an absorbance after transmission through the water.

The calculation of the glucose concentration in the skin tissue is performed from the absorbance after back-scattering at the living body tissue and the absorbance after transmission through the water, which are obtained using the above method. For example, the operational unit 150 includes a measuring object absorbance calculation unit (an absorbance calculation device) 151 and a concentration calculation unit (a concentration calculation device) 152. The measuring object absorbance calculation unit (the absorbance calculation device) 151 obtains an absorbance of the living body tissue with respect to the water that is the reference material. The absorbance of the living body tissue is obtained using, for example, Equation (1):

[Equation 1]

$$\mu_a l - \mu_{aw} d = \mu_{a1} V_1 l + \mu_{a2} V_2 l + \ldots + \mu_{an} V_n l + \mu_{aw}(V_{wl} l - d) \quad (1)$$

In Equation (1), $\mu_a$ denotes the absorption coefficient of the measuring object (the arm part), $\mu_{a1}$, $\mu_{a2}$ and $\mu_{an}$ denote absorption coefficients of components 1, 2 and n of the measuring object, $\mu_{aw}$ denotes the absorption coefficient of the water, $V_1$, $V_2$, and $V_n$ denote concentrations (volume fraction) of the components 1, 2 and n of the measuring object, l denotes an average value of an optical path length of measuring object, d denotes an optical path length of the water, and $V_{wl}$ denotes a concentration (volume fraction) of the water in the living body tissue.

In Equation (1), the absorption coefficients of the components of the measuring object, the absorption coefficient of the water, the concentrations (volume fraction) of the components of the measuring object, and a concentration (volume fraction) of the water in the living body tissue may be replaced with molar absorption coefficients of the components of the measuring object, a molar absorption coefficient of the water, molar concentrations of the components of the measuring object, and a molar concentration of the water in the living body tissue, respectively.

It is preferable that an optical path length d for the water arranged on the reference optical path be a value close to a value obtained by multiplying an average value l of an optical path length for the measuring object by a volume concentration $V_{wl}$ of the water in the living body tissue. This is because the resultant absorbance decreases and an influence of the water occupying most of the living body tissue can be reduced for highly accurate measurement. l may be calculated using, for example, the Monte Carlo method according to a scattering coefficient of the living body tissue in advance and an average value of the measuring object may be used as $V_w$ to determine d.

Simulation using the Monte Carlo method, for example, is performed as follows:

First, photons (beam) are used as a model of an irradiation light and irradiated to a skin model to perform calculation. The photons irradiated to the skin model move in the skin model. In this case, a distance L and a direction θ to a next point to which the photons proceed are determined by a random number R. Calculation of the distance L to the next point to which the photons proceed is performed using the following Equation (2):

[Equation 2]

$$L = \ln(R/\mu_s) \quad (2)$$

In Equation (2), ln(A) indicates a natural logarithm of A. $\mu_s$ denotes a scattering coefficient of the s-th layer (any one of an epidermal layer, a dermal layer, and a subcutaneous tissue layer) of the skin model. Calculation of the direction θ to the next point to which the photons proceed is performed by the following Equation (3).

[Equation 3]

$$\theta = \cos^{-1}\left[\frac{1}{2g}\left\{1 + g^2 - \left(\frac{1-g^2}{1+g-2gR}\right)^2\right\}\right] \quad (3)$$

In Equation (3), g denotes an anisotropy parameter that is an average of a cosine of a scattering angle and the anisotropy parameter of the skin is about 0.9.

The calculations of Equations (2) and (3) are iteratively performed per unit time. Accordingly, the movement path of the photons from the output surface 118a to the input surface 119a can be calculated. Also, the calculation of the movement distance may be performed on a plurality of photons. For example, the movement distance of $10^8$ photons is calculated.

Figure 5:
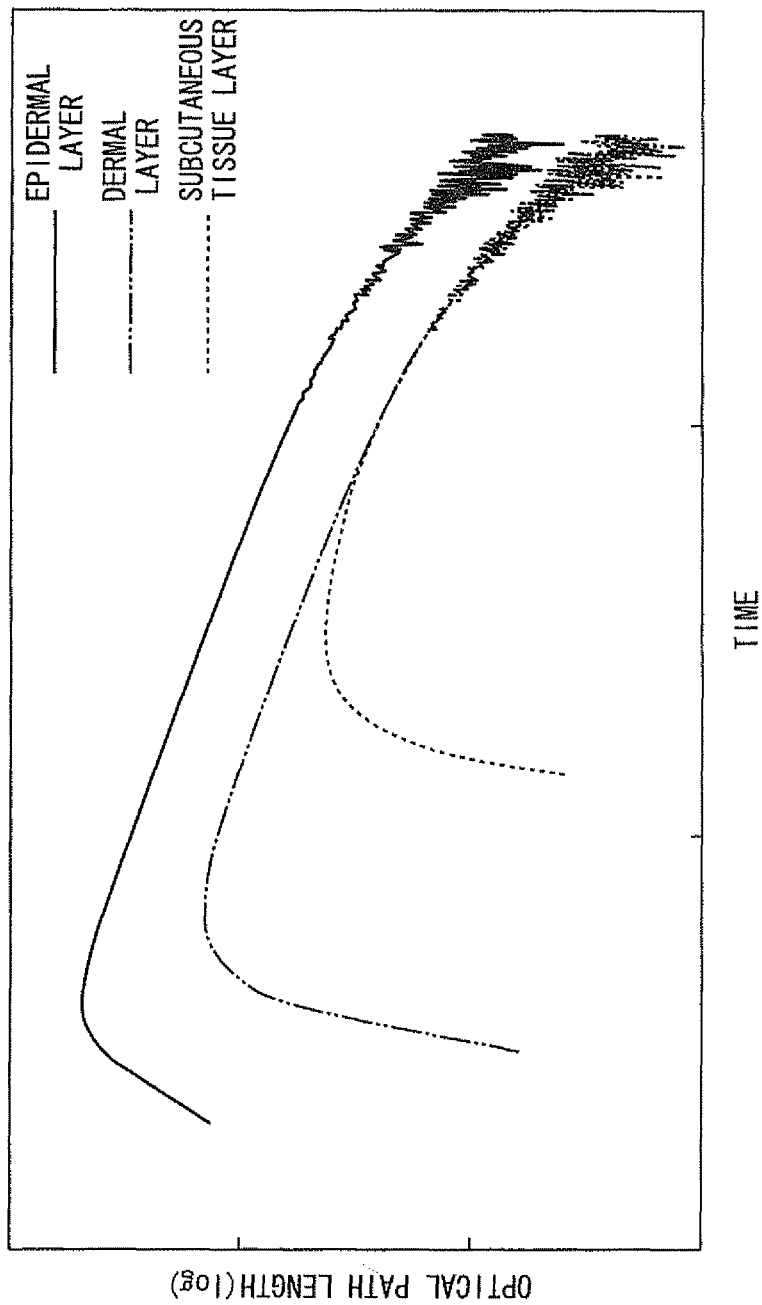
FIG. 5 is a graph showing an example of an optical propagation path length distribution of respective layers of a living body tissue (skin)

FIG. 5 is a graph showing an example of an optical propagation path length distribution of the layers of a living body tissue (skin).

In FIG. 5, a horizontal axis indicates an elapsed time from the irradiation of photons, and a vertical axis indicates a logarithm of the optical path length. Movement paths of photons reaching the light receiving element are classified for each layer through which the movement path passes, and an average length of the movement path of the photons reaching per unit time is calculated for each classified layer. Accordingly, the optical propagation path length distributions of the respective layers of the skin as shown in FIG. 4 can be calculated.

Figure 6:
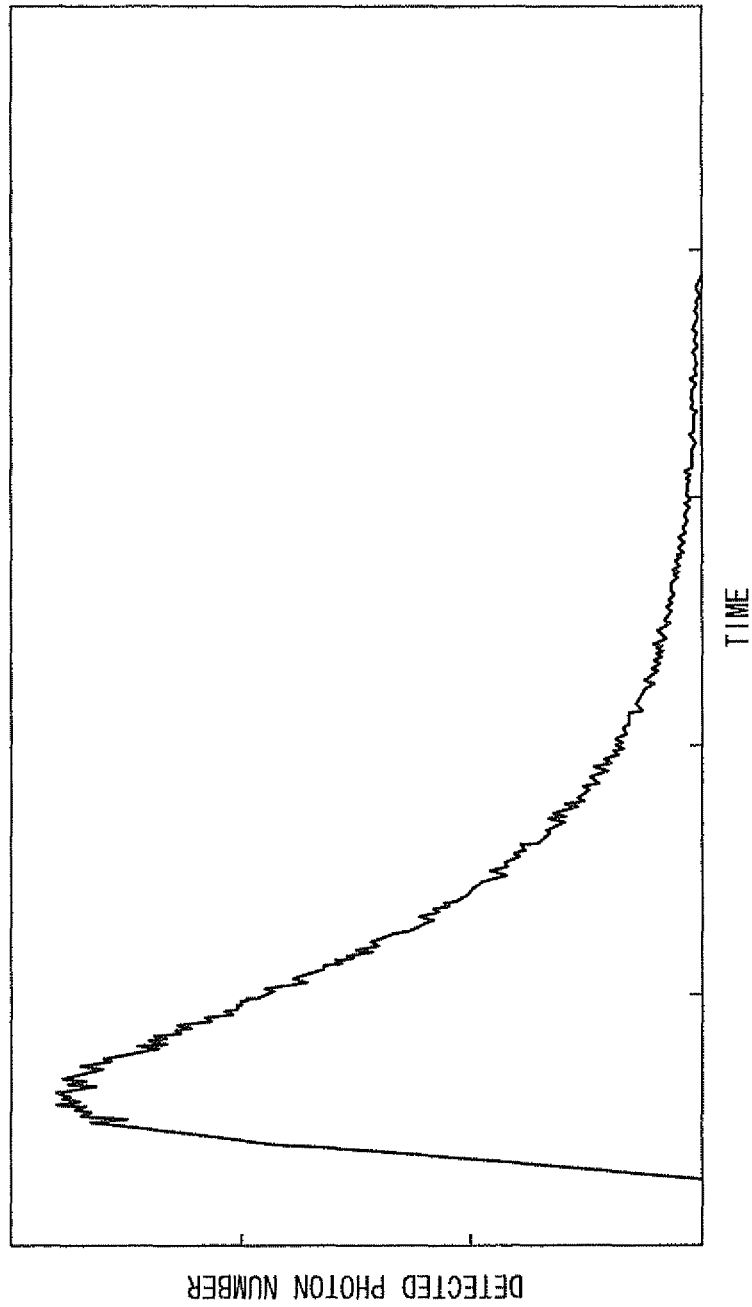
FIG. 6 is a graph showing an example of a time-resolved waveform.

FIG. 6 is a graph showing an example of a time-resolved waveform.

In FIG. 6, a horizontal axis indicates an elapsed time from the irradiation of photons, and a vertical axis indicates the detected photon number by the light receiving element. The number of the photons reaching the light receiving element per unit time is calculated. Accordingly, a time-resolved waveform of the skin model as shown in FIG. 5 can be calculated.

Through the process described above, the optical propagation path length distribution and the time-resolved waveform of the skin model are calculated for a plurality of wavelengths. In this case, the optical propagation path length distribution and the time-resolved waveform may be calculated for a wavelength at which orthogonality of absorption spectra of main components (e.g., water, protein, lipid, glucose) of the skin becomes higher.

Figure 7:
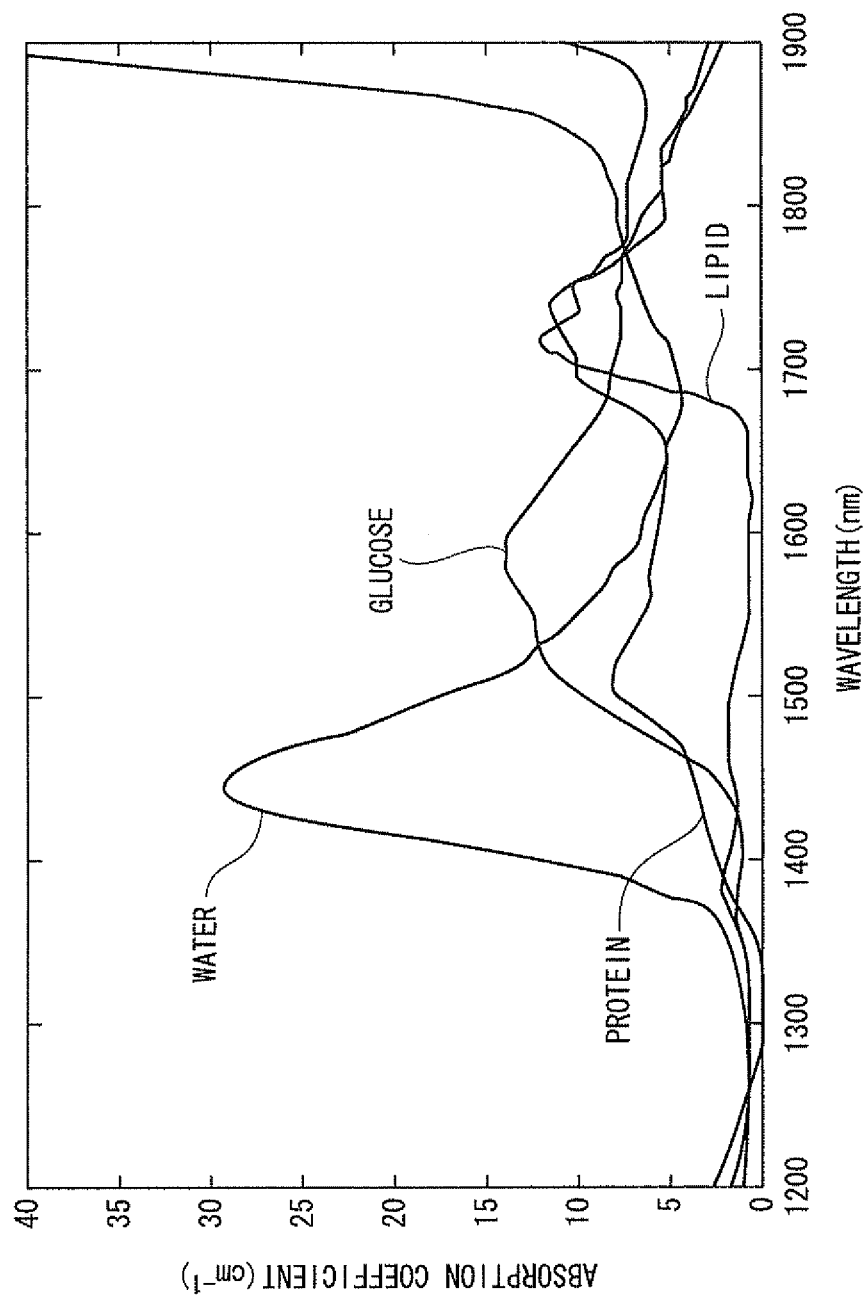
FIG. 7 is a graph showing absorption spectra of main components of the skin.

FIG. 7 is a graph showing absorption spectra of main components of the skin.

In FIG. 7, a horizontal axis indicates a wavelength of an irradiation light, and a vertical axis indicates an absorption coefficient. Referring to FIG. 7, an absorption coefficient of glucose is maximized when the wavelength is 1600 nm, and an absorption coefficient of water is maximized when the wavelength is 1450 nm. Accordingly, for example, the optical propagation path length distribution and the time-resolved waveform may be calculated for the wavelengths 1450 nm or 1600 nm at which orthogonality of the absorption spectra of the main components of the skin becomes higher.

The concentration is obtained by the concentration calculation unit (the concentration calculation device) 152. The concentration calculation can be performed by solving Equation (1) as simultaneous equations corresponding to a plurality of wavelengths. The obtained glucose concentration in the living body tissue is displayed and output on the concentration display unit 160 as a blood sugar level.

Further, the concentration of the living body tissue may be obtained using, for example, multi-variate analysis such as main-component regression analysis.

As described above, according to the concentration determination apparatus and the concentration determination method of the present invention, the liquid (e.g., water) that is the reference material is stored in the liquid tank (storage body), which stores the liquid, and the absorbance of the reference light transmitted through the liquid is referenced with respect to the absorbance of the measurement light back-scattered from the living body tissue that is the measuring object, thereby obtaining an accurate absorbance without being affected by the liquid (e.g., water) contained in the measuring object.

Further, the temperature control plate having excellent thermal conductivity is formed in at least part of the liquid tank (storage body) that contacts the measuring object. Accordingly, the temperature of the water in the liquid tank rises due to the body temperature of the living body tissue that is the measuring object, for example, the human body, through the temperature control plate, such that the temperature of the water can be rapidly the same as the temperature of the living body tissue. An absorption characteristic of the water is sensitive to a temperature, as is well known. However, as in the present embodiment, the temperature of the liquid that is the reference material becomes the same as the temperature of the living body tissue that is the measuring object (a thermal equilibrium state) and then the absorbance is measured, thereby eliminating an error caused by an influence of water in the living body tissue due to a temperature change and performing an accurate concentration determination for the measured material.

(Second Embodiment)

Figure 8:
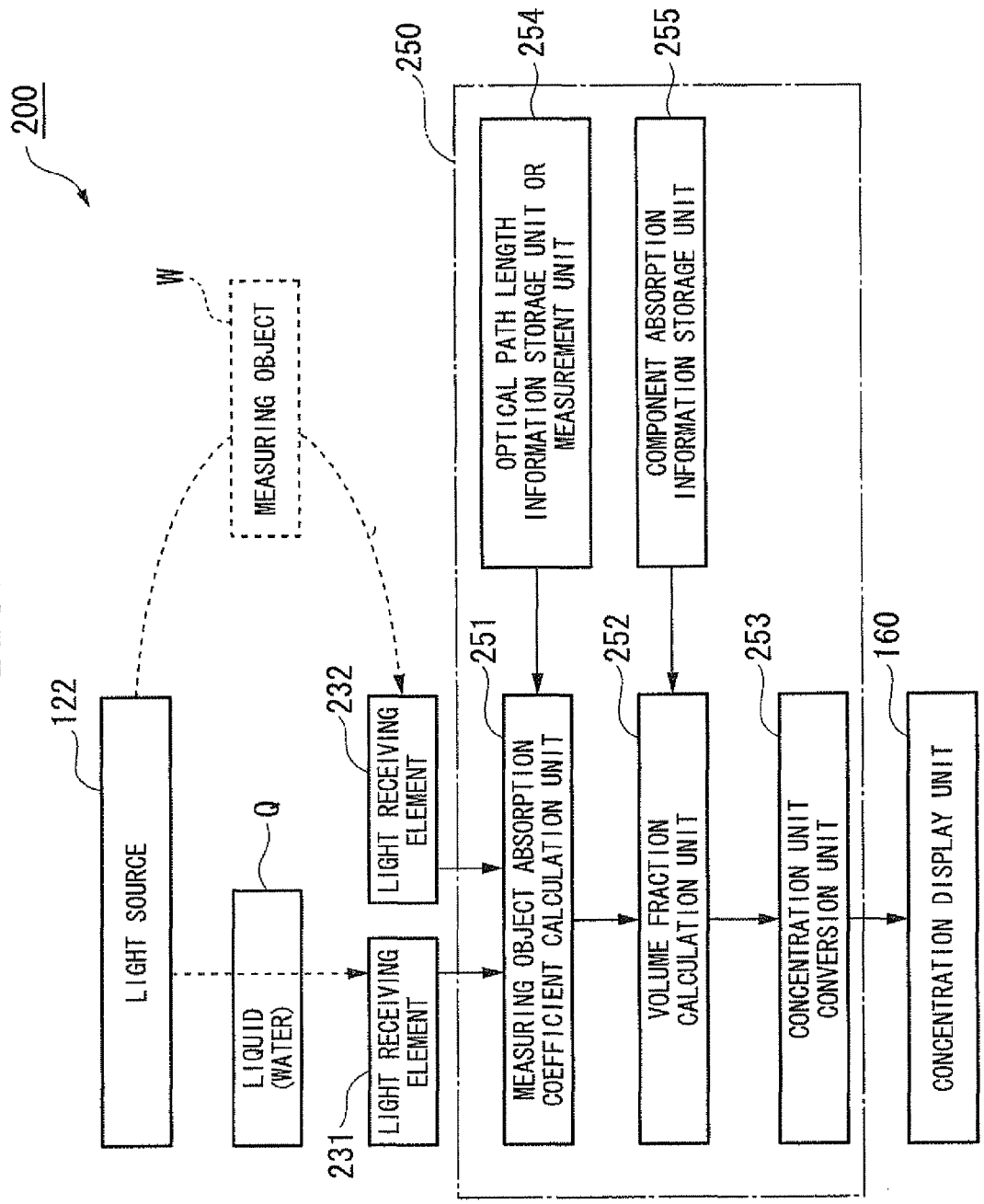
FIG. 8 is a diagram showing a configuration of a concentration determination apparatus in a second embodiment.

FIG. 8 is a schematic block diagram showing a configuration of a blood sugar level measurement apparatus in a second embodiment.

In the second embodiment, a light receiving element 231 for receiving a reference light and a light receiving element 232 for receiving a measurement light are independently formed, unlike the first embodiment described above. An arithmetic unit 250 includes a measuring object absorption coefficient calculation unit 251, a volume fraction calculation unit 252, a concentration unit conversion unit 253, an optical path length information storage unit (an optical path length information measurement unit) 254, and a component absorption information storage unit 255.

In the blood sugar level measurement apparatus 200 of the second embodiment, an absorption coefficient of the measuring object with respect to water (liquid), which is a reference material, is calculated from a measurement light as a back-scattered light from the living body tissue that is the measuring object. An optical path length d for the water is set to l. l can be calculated, for example, using a Monte Carlo method in advance, as in the first embodiment. When l=d, Equation (1) described above may be replaced with Equation (4) shown below. When simultaneous equations for a plurality of wavelengths are solved using Equation (4), the number of wavelength data equations is reduced by one as compared to the first embodiment, which can simplify a procedure (process) of a concentration calculation process.

[Equation 4]

$$\mu_a - \mu_{aw} = (\mu_{a1} - \mu_{aw})V_1 + (\mu_{a2} - \mu_{aw})V_2 + \ldots + (\mu_{an} - \mu_{aw})V_n$$
$$\text{where } V_1 + V_2 + \ldots + V_n + V_w = 1 \quad (4)$$

(Third Embodiment)

Figure 9:
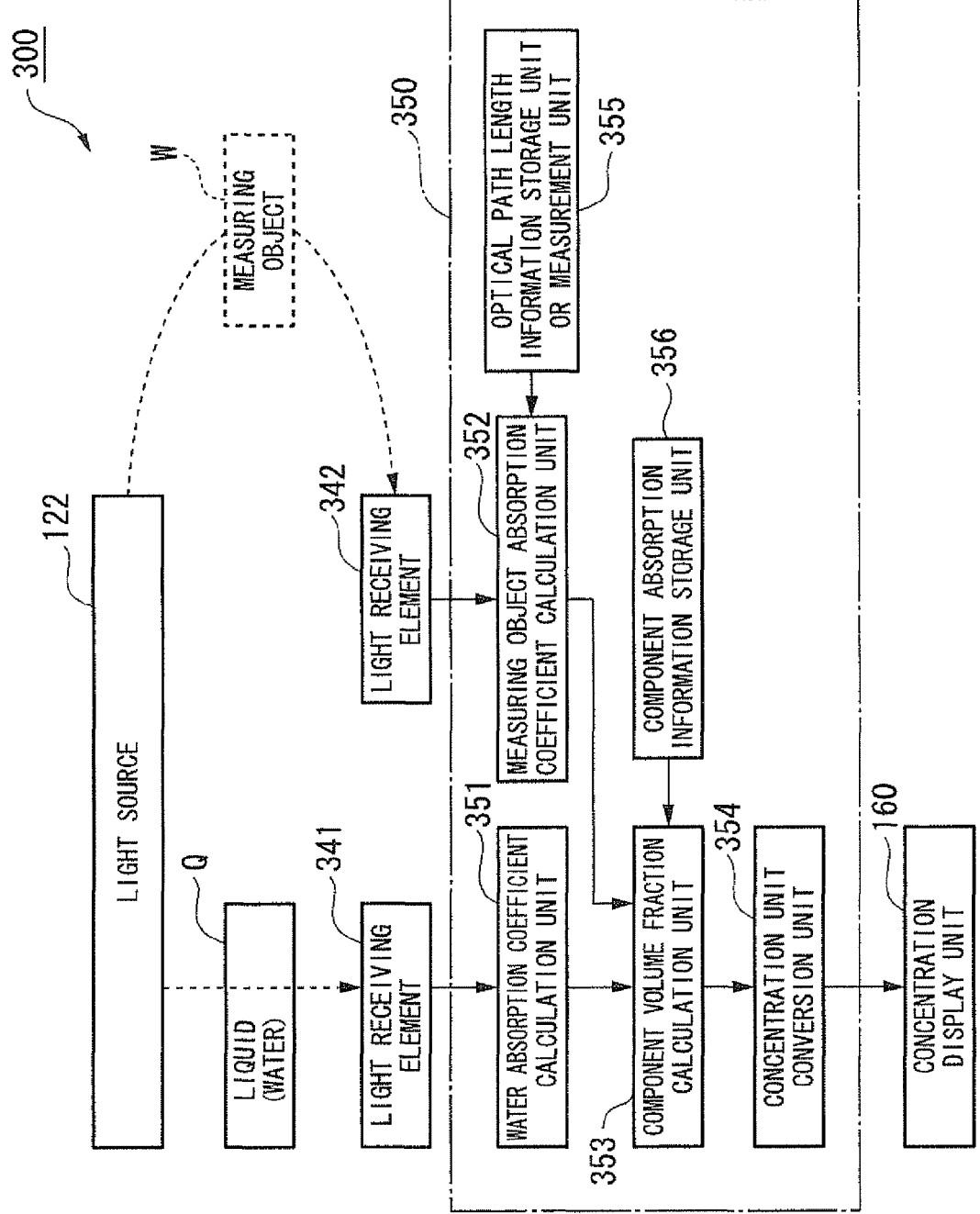
FIG. 9 is a diagram shows a configuration of a concentration determination apparatus in a third embodiment.

FIG. 9 is a schematic block diagram of a configuration of a blood sugar level measurement apparatus in a third embodiment.

In the third embodiment, a light receiving element 341 for receiving a reference light and a light receiving element 342 for receiving a measurement light are independently formed. Further, an arithmetic unit 350 includes a water absorption coefficient calculation unit 351, a measuring object absorption coefficient calculation unit 352, a component volume fraction calculation unit 353, a concentration unit conversion unit 354, an optical path length information storage unit (an optical path length information measurement unit) 355, and a component absorption information storage unit 356.

In the blood sugar level measurement apparatus 300 of the third embodiment, an absorption coefficient of water (liquid) that is a reference material and an absorption coefficient of a living body tissue that is a measuring object are individually calculated, unlike the first embodiment and the second embodiment. The absorption coefficient of the water is calculated by calculating the absorbance of the water from a signal of the light receiving element 341 of the reference light transmitted through the water and using optical path length information of the water.

Similarly, in the calculation of the absorption coefficient of the measuring object (the living body tissue), an absorbance of the living body tissue is calculated from a signal of the light receiving element 342 of the measurement light that is a back-scattered light from the living body tissue. The calculation of the absorption coefficient of the measuring object can be performed by obtaining an absorption coefficient of a portion of the target through time-resolved measurement. If the absorption coefficients of the water and the measuring object are obtained, the calculation of the component concentration may be performed using the same method as in the first embodiment and the second embodiment.

(Fourth Embodiment)

Figure 10A:
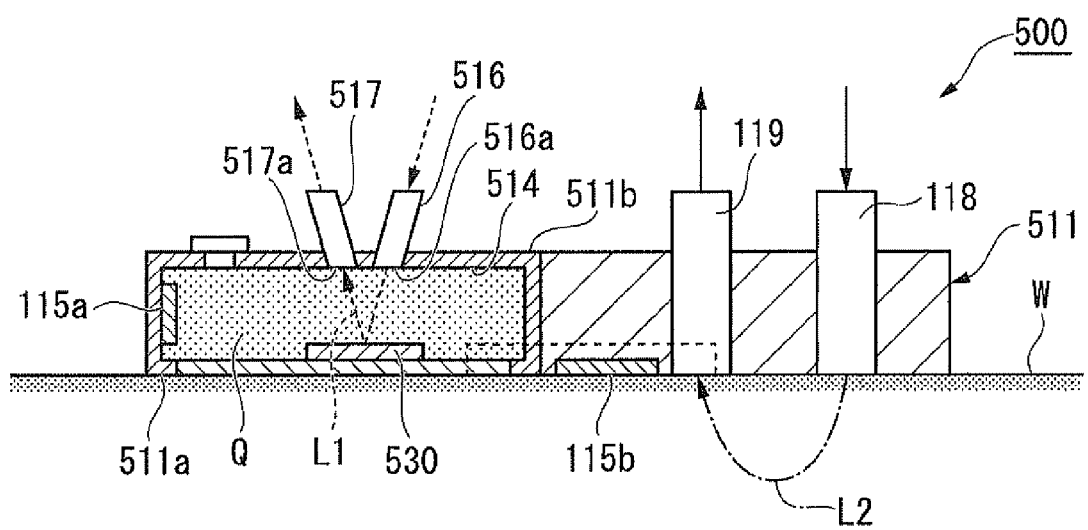
FIG. 10A is a cross-sectional view of a body part in a concentration determination apparatus in a fourth embodiment.
Figure 10B:
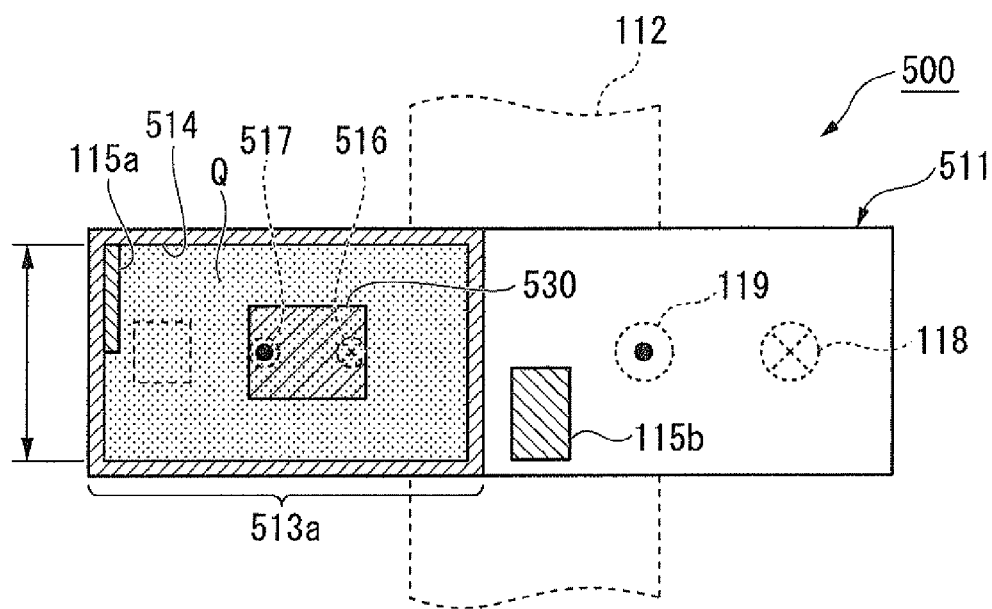
FIG. 10B is a plan view of the body part in the concentration determination apparatus of the fourth embodiment when viewed from above.

FIG. 10A is a cross-sectional view showing a configuration of a body part of a blood sugar level measurement apparatus in a fourth embodiment. FIG. 10B is a plan view of the body part shown in FIG. 10A when viewed from above.

In the fourth embodiment, for example, a hollow liquid tank (a storage body) 514 that liquid (reference material) Q can be injected into and stored in is formed in a first measurement area 513a of the body part 511 in the blood sugar level measurement apparatus 500. In the first measurement area 513a, a first input part 516 is formed in a top surface 511b at an opposite side from a bottom surface 511a of the body part 511 in contact with a living body tissue that is a measuring object so that an output surface 516a of the first input part 516 is exposed to an inner surface of the liquid tank 514. The first input part 516 is, for example, optically connected to a light source.

A first light receiving part 517 is formed to be aligned with the first input part 516 so that an input surface 517a thereof is exposed to the inner surface of the liquid tank 514. The first light receiving part 517 is optically connected to a light receiving element.

An optical reflection film (reflector) 530 is formed to face the output surface 516a and the input surface 517a on a bottom surface of the liquid tank 514 that is the bottom surface 511 a of the body part 511. According to the above-described configuration, a light output from the output surface 516a of the first input part 516 is transmitted through the liquid (water) Q stored in the liquid tank 514 and reaches the optical reflection film (reflector) 530. Also, the light is reflected by the optical reflection film (reflector) 530. The reflected light is transmitted through the liquid (water) Q again and incident on the input surface 517a of the first light receiving part 517.

The first input part 516 may be formed to irradiate light at a predetermined angle with respect to the bottom surface 511a of the body part 511 in advance such that the light reflected by the optical reflection film (reflector) 530 can be accurately incident on the input surface 517a of the first light receiving part 517. For the optical reflection film (reflector) 530, a liquid contact surface 570b of a temperature control plate 570 may be used as an optical reflective surface.

Alternatively, a scattering material such as intralipid may be mixed with the liquid (water) that is the reference material to obtain a scattering characteristic and a back-scattered light may be detected using the light receiving element, instead of forming the above-described optical reflection film (reflector).

(Fifth Embodiment)

Figure 11:
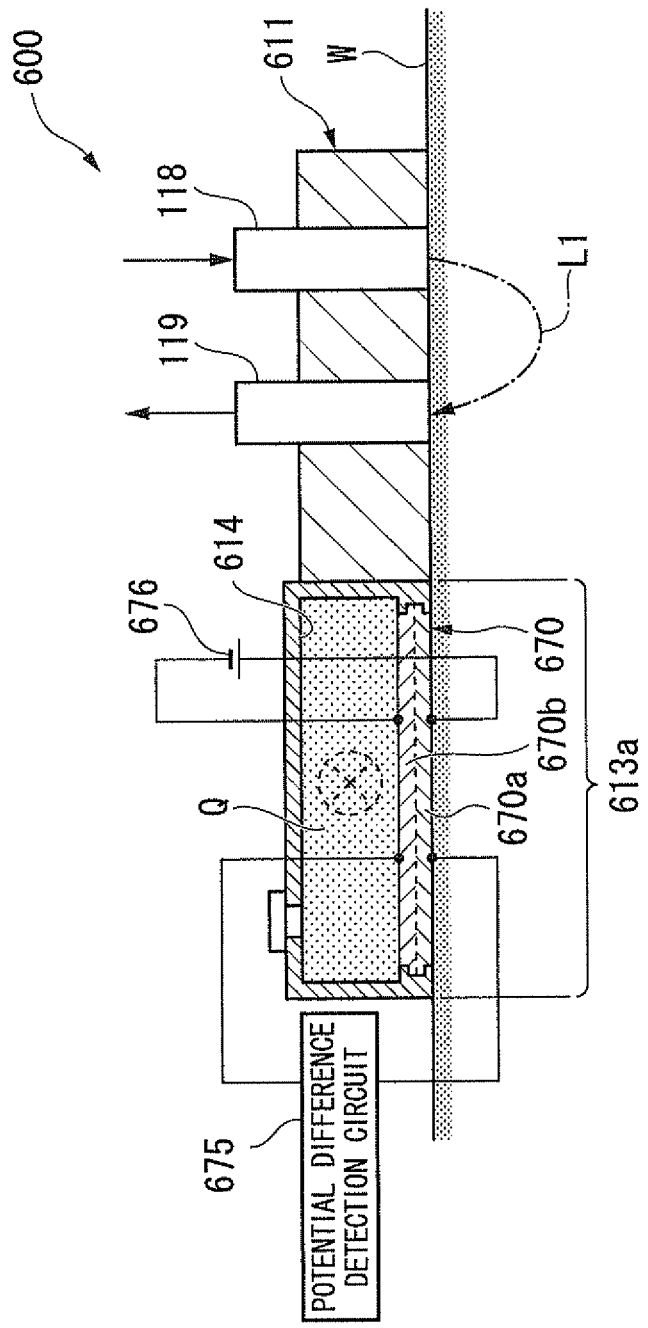
FIG. 11 is a cross-sectional view of a body part in a concentration determination apparatus in a fifth embodiment.

FIG. 11 is a cross-sectional view showing a configuration of a body part of a blood sugar level measurement apparatus in a fifth embodiment.

In the fifth embodiment, for example, a hollow liquid tank (a storage body) 614 that liquid (reference material) Q can be injected into and held in is formed in a first measurement area 613a of a body part 611 in the blood sugar level measurement apparatus 600. A temperature control plate 670 is formed at a side of a bottom surface among wall surfaces partitioning the liquid tank (storage body) 614. In the present embodiment, the temperature control plate 670 is formed of a Peltier element. The Peltier element is formed of, for example, a metal electrode, a p-type semiconductor, and an n-type semiconductor that are alternately connected between upper and lower heat sinks.

When DC current flows into a junction between two types of metals in the above-described Peltier element, the one surface absorbs the heat and heat emission occurs from the opposite surface due to a Peltier effect by which heat moves from one metal to the other metal, which is well known.

In the Peltier element, when there is a temperature difference between the one metal and the other metal, a potential difference is generated between the two types of metals (a Seebeck effect), as is well known. Using this operation, it is possible to detect the temperature difference by measuring the potential difference between the two types of metals.

Using the above-described effect, in the temperature control plate (a temperature detection device or a temperature control device) 670 formed of the Peltier element, a potential difference between a closely contacted surface 670a closely contacted to a surface of an arm part W of a human body that is the living body tissue and a liquid contact surface 670b in contact with the liquid (reference material) Q is determined by a potential difference detection device 675. Also, when there is a potential difference between the closely contacted surface 670a and the liquid contact surface 670b, a circuit connected to the temperature control plate (the temperature detection device or the temperature control device) 670 is switched to a voltage applying device 676.

Also, a voltage from the voltage applying device 676 is applied to the temperature control plate (the temperature detection device or the temperature control device) 670, for example, to heat the liquid contact surface 670b and warm the liquid (reference material) Q. Also, at any time, the circuit is switched to the voltage detection device 675 to measure a potential difference between the closely contacted surface 670a and the liquid contact surface 670b, and the liquid contact surface 670b may be heated until the potential difference between the closely contacted surface 670a and the liquid contact surface 670b is eliminated.

As a Peltier element functioning as both the temperature detection device and the temperature control device is used as the temperature control plate 670, even when there is a temperature difference between the living body tissue that is the measuring object and the liquid (a reference material), the temperature difference can be rapidly eliminated and an accurate concentration determination can be rapidly performed without being affected by a temperature change.

While the preferred embodiments of the present invention have been described above, the present invention is not limited to the embodiments. Addition, omission, substitution, and other modification may be made to the configuration of the present invention without departing from the spirit and scope of the present invention. The present invention is not limited by the above description but limited only by the claims.

100: concentration determination apparatus (blood sugar level measurement apparatus), 114: liquid tank (storage body), 115: temperature detection device, 116: first input part, 117: first light receiving part, 118: second input part, 119: second light receiving part, 151: measuring object absorbance calculation unit (absorbance calculation device), 152: concentration calculation unit (concentration calculation device), 170: temperature control plate, 170a: closely contacted surface, 170b: liquid contact surface.

What is claimed is:

1. A concentration determination apparatus comprising:
   a storage body that holds liquid,
   a temperature control plate constituting the storage body and having one surface forming a closely contacted surface which is closely contacted to a living body tissue and another surface forming a liquid contact surface brought into contact with the liquid,
   a first input light guide that causes a first incident light to be incident on the storage body,
   a first light receiving light guide that receives a reference light transmitted through the liquid from the first input light guide,
   a second input light guide that causes a second incident light to be incident on the living body tissue,
   a second light receiving light guide that receives a measurement light from the second input light guide via the living body tissue,
   a temperature detector that detects a temperature of the liquid and a temperature of the living body tissue,
   a light receiving element that detects a light intensity of the reference light and a light intensity of the measurement light, and
   an operational unit comprises:
      an absorbance calculation device that calculates an absorbance of the liquid and an absorbance of the living body tissue based on the light intensity of the reference light and the light intensity of the measurement light, and a concentration calculation device that compares the absorbance of the liquid with the absorbance of the living body tissue and calculates a concentration of a measured component contained in the living body tissue.

2. The concentration determination apparatus according to claim 1, wherein the liquid is a liquid having a scattering characteristic.

3. The concentration determination apparatus according to claim 2, wherein the liquid is water or liquid corresponding to body fluid.

4. The concentration determination apparatus according to claim 1, wherein the temperature control plate includes a thermal conductor that causes the body temperature of the living body tissue and the liquid temperature of the liquid to be heat-exchanged with each other.

5. The concentration determination apparatus according to claim 1, wherein the storage body further includes a reflector that reflects the first incident light incident from the first input light guide to the first light receiving light guide.

6. The concentration determination apparatus according to claim 1, further comprising a plurality of light sources.

7. The concentration determination apparatus according to claim 1, wherein the storage body further comprises a temperature controller that heats or cools the liquid.

8. The concentration determination apparatus according to claim 1. further comprising:
a light source, and
a spectral unit that divides light irradiated from the light source toward the first input light guide and the second input light guide.

9. The concentration determination apparatus according to claim 1, wherein an optical path length for the reference light from the first input light guide to the first light receiving light guide is set to be the same as an optical path length for the measurement light from the second input light guide to the second light receiving light guide.

10. The concentration determination apparatus according to claim 1, wherein the absorbance calculation device respectively detects the absorbance of the liquid and the absorbance of the living body tissue if a difference between the temperature of the living body tissue and the temperature of the liquid is within a predetermined value.

11. The concentration determination apparatus according to claim 10, wherein the predetermined value is 0.1° C.

12. A concentration determination method using a concentration determination apparatus comprising
a storage body that holds liquid,
a temperature control plate constituting the storage body and having one surface forming a closely contacted surface which is closely contacted to a living body tissue and the other surface forming a liquid contact surface brought into contact with the liquid,
a first input light guide that causes a first incident light to be incident on the storage body,
a first light receiving light guide that receives a reference light transmitted through the liquid from the first input light guide.
a second input light guide that causes a second incident light to be incident on the living body tissue,
a second light receiving light guide that receives a measurement light from the second input light guide via the living body tissue,
a temperature detector that detects a temperature of the liquid and a temperature of the living body tissue,
a light receiving element that detects a light intensity of the reference light and a light intensity of the measurement light, and
an operational unit comprises:
an absorbance calculation device that calculates an absorbance of the liquid and an absorbance of the living body tissue based on a light intensity of the reference light and a light intensity of the measurement light, and
a concentration calculator that compares the absorbance of the liquid with the absorbance of the living body tissue and calculates a concentration of a measured component contained in the living body tissue,
wherein:
the measurement light is light from the second incident light back-scattered in the living body tissue, and
the method comprises processes of:
equilibrating the temperatures so that a difference between the body temperature of the living body tissue and the liquid temperature of the liquid is within 0.1° C.;
measuring the absorbance of the liquid based on the light intensity of the reference light;
measuring the absorbance of the living body tissue based on the light intensity of the measurement light; and
using the absorbance of the liquid as a reference and calculating the concentration of the measured component contained in the living body tissue from the absorbance of the living body tissue.

13. The concentration determination method according to claim 12, wherein the first incident light and the second incident light are short pulsed lights.

* * * * *